(12) United States Patent
Peters

(10) Patent No.: US 8,425,397 B2
(45) Date of Patent: *Apr. 23, 2013

(54) PERCUTANEOUS GAS-LINE

(75) Inventor: William Suttle Peters, Auckland (NZ)

(73) Assignee: Sunshine Heart Company PTY Ltd, Crows Nest NSW (AU)

(*) Notice: Subject to any disclaimer, the term of this patent is extended or adjusted under 35 U.S.C. 154(b) by 0 days.

This patent is subject to a terminal disclaimer.

(21) Appl. No.: 12/962,558

(22) Filed: Dec. 7, 2010

(65) Prior Publication Data

US 2011/0275883 A1   Nov. 10, 2011

Related U.S. Application Data

(63) Continuation of application No. 10/595,603, filed as application No. PCT/AU2004/001485 on Oct. 28, 2004, now Pat. No. 7,887,478.

(51) Int. Cl.
*A61M 1/10* (2006.01)
*A61M 5/00* (2006.01)

(52) U.S. Cl.
USPC .................................. 600/16; 600/17; 600/18

(58) Field of Classification Search ............... 600/16
See application file for complete search history.

(56) References Cited

U.S. PATENT DOCUMENTS

| 283,660 A | 8/1883 | Reed |
|---|---|---|
| 929,571 A | 7/1909 | Dubied |
| 1,576,397 A | 3/1926 | Yanagi |
| 1,719,316 A | 7/1929 | Appleton |
| 3,467,077 A | 9/1969 | Cohen |
| 3,552,383 A | 1/1971 | Krueger et al. |
| 3,597,766 A | 8/1971 | Buck |
| 4,014,318 A | 3/1977 | Dockum et al. |

(Continued)

FOREIGN PATENT DOCUMENTS

| AU | 2003277983 B2 | 6/2008 |
|---|---|---|
| DE | 1541311 A1 | 9/1969 |

(Continued)

OTHER PUBLICATIONS

Hiroshi Odaguchi et al., "Experimental Study of Extraaortic Balloon Counterpulsation as a Bridge to Other Mechanical Assists" ASAIO Journal, pp. 190-194, vol. 42, No. 3, Lippincott Williams & Wilkins/ASAIO, Hagerstown, MD, May 1, 1996.

(Continued)

*Primary Examiner* — Allen Porter, Jr.
(74) *Attorney, Agent, or Firm* — Davis, Brown, Koehn, Shors & Roberts, P.C.; Sean D. Solberg

(57) ABSTRACT

A percutaneous gas-line (10) for a medical device (14). The gas-line including a first gas-line part (10*a*) and a second gas-line part (10*b*). The first gas-line part (10*a*) is adapted to be wholly implanted in a patient and has a first end (10*a*') adapted for sealing connection to the medical device (14) and a second end (10*a*'') with a connection fitting (20). The second gas-line part (10*b*) is adapted to be part-implanted and part-external and has a first (external) end (10*b*') adapted for sealing connection to an external driver (12) and a second (implanted) end (10*b*'') adapted for removable sealing connection with the connection fitting (20) on the second end (10*a*'') of the first gas-line part (10*a*).

20 Claims, 2 Drawing Sheets

U.S. PATENT DOCUMENTS

| | | |
|---|---|---|
| 4,046,137 A | 9/1977 | Curless |
| 4,051,840 A | 10/1977 | Kantrowitz et al. |
| 4,176,411 A | 12/1979 | Runge |
| 4,195,623 A | 4/1980 | Zeff et al. |
| 4,236,482 A | 12/1980 | Gingerich et al. |
| 4,256,094 A | 3/1981 | Kapp et al. |
| 4,277,706 A | 7/1981 | Isaacson |
| 4,304,225 A | 12/1981 | Freeman |
| 4,454,891 A | 6/1984 | Dreibelbis et al. |
| 4,457,673 A | 7/1984 | Conley et al. |
| 4,459,977 A | 7/1984 | Pizon et al. |
| 4,515,587 A | 5/1985 | Schiff |
| 4,583,523 A | 4/1986 | Kleinke et al. |
| 4,594,731 A | 6/1986 | Lewkowicz |
| 4,630,597 A | 12/1986 | Kantrowitz et al. |
| 4,676,482 A | 6/1987 | Reece et al. |
| 4,697,574 A | 10/1987 | Karcher et al. |
| 4,763,646 A | 8/1988 | Lekholm |
| 4,771,765 A | 9/1988 | Choy et al. |
| 4,809,676 A | 3/1989 | Freeman |
| 4,813,952 A | 3/1989 | Khalafalla |
| 4,822,357 A | 4/1989 | Forster et al. |
| 4,881,939 A | 11/1989 | Newman |
| 4,886,490 A | 12/1989 | Shiber |
| 4,957,477 A | 9/1990 | Lundback |
| 4,979,936 A | 12/1990 | Stephenson et al. |
| 5,089,017 A | 2/1992 | Young et al. |
| 5,169,378 A | 12/1992 | Figuera |
| 5,197,980 A | 3/1993 | Gorshkov et al. |
| 5,205,810 A | 4/1993 | Guiraudon et al. |
| 5,222,980 A | 6/1993 | Gealow |
| 5,267,940 A | 12/1993 | Moulder |
| 5,273,518 A | 12/1993 | Lee et al. |
| 5,290,249 A | 3/1994 | Foster et al. |
| 5,300,111 A | 4/1994 | Panton et al. |
| 5,337,752 A | 8/1994 | Reeves |
| 5,344,385 A | 9/1994 | Buck et al. |
| 5,360,445 A | 11/1994 | Goldowsky |
| 5,372,573 A | 12/1994 | Habib |
| 5,411,535 A | 5/1995 | Jujll |
| 5,429,584 A | 7/1995 | Chiu |
| 5,447,523 A | 9/1995 | Schaldach |
| 5,453,076 A | 9/1995 | Kiyota et al. |
| 5,511,551 A | 4/1996 | Sano et al. |
| 5,554,177 A | 9/1996 | Kieval et al. |
| 5,568,544 A | 10/1996 | Keeler |
| 5,569,156 A | 10/1996 | Mussivand |
| 5,593,414 A | 1/1997 | Shipp et al. |
| 5,607,378 A | 3/1997 | Winston |
| 5,647,380 A | 7/1997 | Campbell et al. |
| 5,651,059 A | 7/1997 | Morgan et al. |
| 5,722,930 A | 3/1998 | Larson, Jr. et al. |
| 5,792,195 A | 8/1998 | Carlson et al. |
| 5,814,012 A | 9/1998 | Fleenor et al. |
| 5,820,542 A | 10/1998 | Dobak, III et al. |
| 5,827,171 A | 10/1998 | Dobak, III et al. |
| 5,843,170 A | 12/1998 | Ahn |
| 5,953,389 A | 9/1999 | Pruett et al. |
| 5,975,140 A | 11/1999 | Lin |
| 5,980,488 A | 11/1999 | Thorne |
| 6,030,336 A | 2/2000 | Franchi |
| 6,045,496 A | 4/2000 | Pacella et al. |
| 6,066,085 A | 5/2000 | Heilman et al. |
| 6,066,086 A | 5/2000 | Antaki |
| 6,118,776 A | 9/2000 | Berman |
| 6,132,363 A * | 10/2000 | Freed et al. .................. 600/16 |
| 6,132,636 A | 10/2000 | Singh et al. |
| 6,210,318 B1 | 4/2001 | Lederman |
| 6,210,319 B1 | 4/2001 | Williams et al. |
| 6,226,843 B1 | 5/2001 | Crainich |
| 6,251,061 B1 | 6/2001 | Hastings et al. |
| 6,406,422 B1 | 6/2002 | Landesberg |
| 6,415,693 B1 | 7/2002 | McCanne |
| 6,432,039 B1 | 8/2002 | Wardle |
| 6,471,633 B1 | 10/2002 | Freed |
| 6,553,263 B1 | 4/2003 | Meadows et al. |
| 6,572,534 B1 | 6/2003 | Milbocker et al. |
| 6,585,635 B1 | 7/2003 | Aldrich |
| 6,604,140 B1 | 8/2003 | Beck |
| 6,616,596 B1 | 9/2003 | Milbocker |
| 6,626,821 B1 | 9/2003 | Kung et al. |
| 6,643,548 B1 | 11/2003 | Mai et al. |
| 6,792,308 B2 | 9/2004 | Corbucci |
| 6,808,483 B1 | 10/2004 | Ortiz et al. |
| 6,808,484 B1 | 10/2004 | Peters et al. |
| 6,984,201 B2 | 1/2006 | Khaghani et al. |
| 7,169,109 B2 | 1/2007 | Jansen et al. |
| 7,347,811 B2 | 3/2008 | Peters et al. |
| 7,357,771 B2 | 4/2008 | Peters et al. |
| 7,360,558 B1 | 4/2008 | Chen et al. |
| 7,513,864 B2 | 4/2009 | Kantrowitz et al. |
| 7,740,575 B2 | 6/2010 | Peters et al. |
| 7,765,003 B2 | 7/2010 | Peters et al. |
| 7,887,478 B2 * | 2/2011 | Peters .......................... 600/16 |
| 2001/0016676 A1 | 8/2001 | Williams et al. |
| 2003/0028599 A1 | 2/2003 | Kolsky |
| 2003/0105497 A1 | 6/2003 | Zhu et al. |
| 2004/0010180 A1 | 1/2004 | Scorvo |
| 2004/0073080 A1 | 4/2004 | Peters et al. |
| 2004/0097783 A1 | 5/2004 | Peters et al. |
| 2004/0097784 A1 | 5/2004 | Peters et al. |
| 2004/0147803 A1 | 7/2004 | Hegde et al. |
| 2004/0152945 A1 | 8/2004 | Kantrowitz et al. |
| 2004/0230090 A1 | 11/2004 | Hegde |
| 2006/0052866 A1 | 3/2006 | Gilles et al. |
| 2006/0135134 A1 | 6/2006 | Mezhvinsky et al. |
| 2007/0021830 A1 | 1/2007 | Peters |
| 2007/0093684 A1 | 4/2007 | Peters |
| 2007/0129796 A1 | 6/2007 | Miller |
| 2007/0135677 A1 | 6/2007 | Miller et al. |
| 2007/0167898 A1 | 7/2007 | Peters et al. |
| 2008/0027270 A1 | 1/2008 | Peters et al. |
| 2008/0139873 A1 | 6/2008 | Peters et al. |
| 2008/0167515 A1 | 7/2008 | Peters et al. |
| 2008/0194905 A1 | 8/2008 | Walsh |
| 2010/0292528 A1 | 11/2010 | De Plater et al. |
| 2010/0324354 A1 | 12/2010 | Peters |
| 2011/0196467 A1 | 8/2011 | Miller et al. |
| 2011/0270331 A1 | 11/2011 | Peters et al. |
| 2011/0275883 A1 | 11/2011 | Peters |
| 2011/0288367 A1 | 11/2011 | Miller |

FOREIGN PATENT DOCUMENTS

| | | |
|---|---|---|
| EP | 0080348 B1 | 5/1988 |
| EP | 0363203 A2 | 4/1990 |
| EP | 0216042 B1 | 3/1991 |
| EP | 0601804 A1 | 6/1994 |
| EP | 0364799 A2 | 5/1995 |
| EP | 1129736 A1 | 9/2001 |
| FR | 2458288 A1 | 1/1981 |
| FR | 2645739 A1 | 10/1990 |
| FR | 2767874 A1 | 3/1999 |
| GB | 2422114 B | 4/2008 |
| JP | 6510461 A | 11/1994 |
| JP | 9502376 A | 3/1997 |
| JP | 9503933 A | 4/1997 |
| JP | 10328297 A | 12/1998 |
| JP | 11285529 A | 10/1999 |
| JP | 2000000299 A | 1/2000 |
| JP | 2000510006 T | 8/2000 |
| JP | 2001276213 A | 10/2001 |
| JP | 2003135497 A | 5/2003 |
| WO | WO9015630 A1 | 12/1990 |
| WO | WO9208500 A1 | 5/1992 |
| WO | WO9308874 A1 | 5/1993 |
| WO | WO9505122 A1 | 2/1995 |
| WO | WO9528127 A1 | 10/1995 |
| WO | WO9740755 A1 | 11/1997 |
| WO | WO9805289 A1 | 2/1998 |
| WO | WO9814239 A1 | 4/1998 |
| WO | WO9851367 A1 | 11/1998 |
| WO | WO9902213 A1 | 1/1999 |
| WO | WO9904833 A1 | 2/1999 |
| WO | WO9945981 A1 | 9/1999 |
| WO | WO0012168 A1 | 3/2000 |
| WO | WO0076288 A2 | 12/2000 |
| WO | WO0113974 A2 | 3/2001 |

| | | |
|---|---|---|
| WO | WO0183001 A1 | 11/2001 |
| WO | WO0224254 A2 | 3/2002 |
| WO | WO0224255 A1 | 3/2002 |
| WO | WO02076305 A1 | 10/2002 |
| WO | WO03011365 A1 | 2/2003 |
| WO | WO03028787 A1 | 4/2003 |
| WO | WO2004045677 A1 | 6/2004 |
| WO | WO2005041783 A1 | 5/2005 |
| WO | WO2005042063 A1 | 5/2005 |
| WO | WO2005044338 A1 | 5/2005 |
| WO | WO2005110512 A1 | 11/2005 |
| WO | WO2008053469 A2 | 5/2008 |
| WO | WO2008071223 A1 | 6/2008 |

OTHER PUBLICATIONS

International Preliminary Examination Report issued in PCT/AU2001/01187, completed May 2, 2002, 4 pages.

International Preliminary Examination Report issued in PCT/AU2002/000974, completed Aug. 11, 2003, 8 pages.

International Preliminary Examination Report issued in PCT/AU2003/001450, completed Mar. 2, 2005, 4 pages.

International Preliminary Report on patentability, Chapter II, issued in PCT/AU2007/001188, completed Mar. 11, 2008, 8 pages.

International Prelminary Examination Report issued in PCT/AU2003/001458, completed Mar. 7, 2005, 7 pages.

International Search Report and Written Opinion issued in PCT/AU2004/001483, mailed Nov. 26, 2004, 5 pages.

International Search Report and Written Opinion issued in PCT/AU2004/001484, mailed Nov. 29, 2004, 5 pages.

International Search Report and Written Opinion issued in PCT/AU2004/001486, mailed Jan. 6, 2005, 7 pages.

International Search Report and Written Opinion issued in PCT/AU2004/01485, mailed Feb. 7, 2005, 6 pages.

International Search Report and Written Opinion issued in PCT/AU2004/01487, mailed Jan. 27, 2005, 12 pages.

International Search Report and Written Opinion issued in PCT/AU2004/01488, mailed Dec. 15, 2004, 6 pages.

International Search Report and Written Opinion issued in PCT/AU2007/001188, mailed Oct. 4, 2007, 12 pages.

International Search Report issued in PCT/AU00/00654, mailed Aug. 18, 2000, 5 pages.

International Search Report issued in PCT/AU2001/01187, mailed Nov. 5, 2001, 3 pages.

International Search Report issued in PCT/AU2002/000974, mailed Oct. 11, 2002, 5 pages.

International Search Report issued in PCT/AU2003/001450, mailed Feb. 2, 2004, 2 pages.

International Search Report issued in PCT/AU2003/001458, mailed Feb. 5, 2004, 5 pages.

J.L. Stewart, "Aortic Cuff a Cardiac Assistance Device", Polytechnic Institute of Brooklyn, 1968, pp. 9-108.

Luisada et al., On the Function of the Aortic Valve and the Mechanism of the First and Second Sounds, Japanese Heart Journal, vol. 18(1), Jan. 1977, pp. 81-91.

Office Action issued in JP Application No. 2004-552261, dated Mar. 2, 2010.

Office Action issued in JP Application No. 22006-53700, dispatched Jun. 22, 2010, with English translation, 12 pages.

Seymour Furman et al., "Cardiac Support by Periaortic Diastolic Augmentation", New York Journal of Medicine, Aug. 1, 1970, pp. 1964-1969.

Supplemental European Search Report issued in EP 01971489, completed Nov. 22, 2006, 4 pages.

Supplemental European Search Report issued in EP 04789625, mailed Nov. 18, 2009, 6 pages.

Supplemental European Search Report issued in EP App No. 02748447, Feb. 6, 2007, 6 pages.

Supplemental European Search Report issued in EP App. No. 04789624, mailed Mar. 6, 2008, 7 pages.

Supplemental European Search Report issued in EP Application 00934813, mailed Oct. 19, 2006, 2 pages.

Use of Heart Valve Sounds as Input to Cardiac Assist Devices, Research Disclosures, Mar. 1995.

\* cited by examiner

PERCUTANEOUS GAS-LINE

CROSS-REFERENCE TO RELATED APPLICATION

This application is a continuation of U.S. patent application Ser. No. 10/595,603, filed Apr. 28, 2006, now U.S. Pat. No. 7,887,478 which is the U.S. national stage of PCT Application PCT/AU04/01485, filed on Oct. 28, 2004, which claims priority to Australian Provisional Application No. 20030906067, filed on Oct. 31, 2003, all of which are hereby incorporated herein by reference in their entireties.

TECHNICAL FIELD

The present invention relates generally to a heart assist device, system and method and more particularly to a percutaneous gas-line for an implanted medical device such as a left ventricular assist device (LVAD), or counter-pulsation or co-pulsation heart assist device and to a heart assist device incorporating such a gas-line.

BACKGROUND

International PCT patent application no. PCT/US00/22992 (WO 01/13974) discloses a gas-driven device heart assist device, that requires a percutaneous positioned gas-line.

U.S. Pat. No. 6,132,363 discloses a percutaneous access device (PAD) system, that allows both gas and electrical transmission, that utilises an intermediary connector piece that has the patient's own fibroblasts cultured onto the hub of the PAD. This has the proposed advantage of reducing infection. However, its disadvantages include its large size, inflexible nature, and that implantation is a two or three staged procedure. Specifically, implantation involves making a large skin biopsy, isolating the fibroblasts from the biopsy and growing the cells, then culturing them onto the device (which is a 10 day process). When the culturing process has been completed, the PAD can be implanted in the abdomen, and then the counterpulsation device implanted.

It is an object of the present invention to provide an improved percutaneous gas-line that, at least in preferred embodiments, requires no antecedent preparation and has a low risk profile for infection, but which allows remedial action to be taken in the event that gas-line infection occurs. It is well known that infection related to percutaneous lines in general is influenced by the diameter, flexibility and nature of the material. As such, a smaller, more flexible and soft (particularly Silicone) material are most advantageous in reducing infection—this is in direct contrast to the PAD as disclosed above.

It is a further object to provide a gas line for a heart assist device which gas line incorporates an ECG lead to provide for monitoring of the heart internally of the patient's body to control the operation of the heart assist device.

SUMMARY

Accordingly, in a first aspect, the present invention provides a percutaneous gas-line for a medical device, the gas-line including:
a first gas-line part adapted to be wholly implanted in a patient and having a first end adapted for sealing connection to the medical device and a second end with a connection fitting; and
a second gas-line part adapted to be part-implanted and part-external and having a first (external) end adapted for sealing connection to an external driver and a second (implanted) end adapted for removable sealing connection with the connection fitting on the second end of the first gas-line part.

The second gas-line part is preferably further adapted to be removable, for replacement, in the presence of persistent exit-site infection or damage to the external part.

The medical device is preferably a heart assist device, more preferably a left ventricular assist device (LVAD), or a counter-pulsation or co-pulsation heart assist device.

The first (external) end of the second gas line is preferably removably connected to the external driver.

In preferred embodiments of the invention, an ECG lead adapted to connect a patient's heart with a control system for a heart assist device utilising the gas line according to this invention is incorporated into the first gas line part and/or the second gas line part.

The second gas-line part is preferably constructed to have a minimal outside diameter, more preferably less than 7 mm, and has high flexibility and a resistance to kinking or collapsing. The second gas-line part is preferably made of a soft biocompatible, biostable material, such as silicone 45-65A durometer. This gas-line part may be wire-wound internally to allow thin wall and kink/collapse resistance.

The connection fitting is preferably a Luer-lock or similar gas-tight fitting.

The first and/or second gas-line parts preferably have a fluffy polyester, or similar, collar over about a short section (eg. 20-50 mm) of their implanted length. The collar being adapted to encourage sub-cuateous tissue ingrowth to help reduce any movement of the gas-line in situ—the collar is preferably at least 20 mm from the percutaneous exit site.

(1) recognising a persistent exit-site infection;
(2) disconnecting the second gas-line part from the first gas-line part;
(3) removing the second gas-line part from the patient; and
(4) connecting a sterile second gas-line part to the first gas-line part wherein the fresh second gas-line part is inserted through a fresh exit-site that is remote to the infected exit-site.

It will also be understood by persons skilled in the art that the fresh second gas-line part is inserted through an implant tunnel that is also substantially remote from the existing implant tunnel.

Alternatively, after step (3), the first gas-line part (and the implanted ECG cable, if it is attached to a corresponding interconnect cable associated with the second gas-line part) is sealed and wounds are closed to allow healing to occur (which may include prolonged treatment with antibiotics), at this time the device is non-functional, but can, at a later time, be made functional by re-implanting the second part and sealing attaching it to the first part.

In a third aspect, the present invention provides a gas line for connecting an inflatable heart assist actuator to a driver therefore, the gas line having a first end operatively connected to the inflatable actuator and a second end connectable, directly or indirectly through an extension gas line, to the driver for the heart assist actuator, the gas line having attached to it an ECG lead, the ECG lead having a first end adapted for connection to the heart of a patient and a second end adapted for connection to the driver or a controller for the driver, the attachment between the gas lead and the ECG lead being such that they are adapted to pass through the skin of a patient as a single element.

BRIEF DESCRIPTION OF THE DRAWINGS

A preferred embodiment of the invention will now be described, by way of an example only, with reference to the accompanying drawing in which.

DETAILED DESCRIPTION

Figure 1:
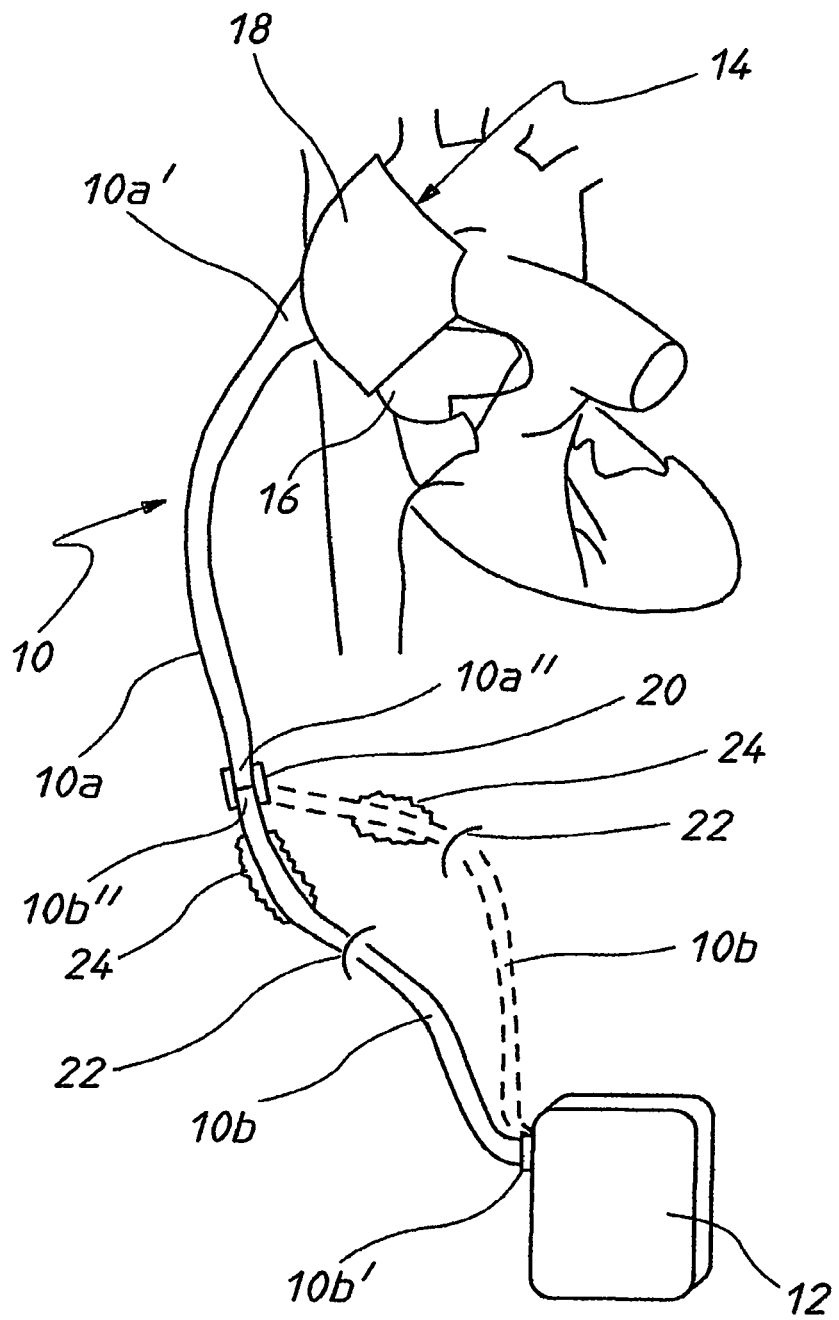
FIG. 1 is a schematic view of a percutaneous gas-line according to an embodiment of the invention, connected between an implanted heart assist device and an external driver.

FIG. 1 shows a percutaneous gas-line 10 according to a first embodiment of the invention. The gas-line 10 has a first part 10a and a second part 10b.

The gas-line 10 connects an external gas driver 12 to a left ventricle heart assist device 14, which is positioned around a patient's aorta 16. The heart assist device 14 comprises a balloon (not shown), a bushing (not shown), and a wrap 18 to hold the balloon in position around the aorta 16.

The first part 10a of the gas-line 10 has a first end 10a' sealingly connected to the bushing and in gas communication with the balloon. The first part 10a of the gas-line 10 also has a second end 10a" with a gas-tight Leur-lock fitting 20 thereon. The first part 10a of the gas-line 10 is made of a polyurethane-polysiloxane block co-polymer similar to that used to form the balloon and bushing.

The second part 10b of the gas-line 10 is shown positioned percutaneous through an exit site 22. The external/un-implanted portion of the second part 10b has a first end 10b' that is connected to the external driver 12 with a gas tight but removable fitting. The second gas-line part 10b also has a second end 10b" connected to the second end 10a" of the first part 10a at the Luer fitting 20. The implanted portion of the second part 10b also has about it a polyester collar 24 for anchoring the gas-line subcutaneously approx 20-50 mm from an exit site 22.

The second part 10b can be made of a different material to the first part 10a. It is preferably made of silicone or silicone-polyurethane co-polymer. The second part 10b can also be more flexible than the first part 10a and can be wire-wound.

In the event that the external part of the gas-line 10 is damaged in every-day use, or if a persistent infection develops at the exit site 24, then the second part 10b is able to be exchanged for a fresh/new (sterilised) second part 10b which is brought out of the patient via a new exit-site 24 (see phantom lines). As this can be done without need to replace the whole heart assist device arrangement, the surgery is minimal. More particularly, the surgery only involves a small incision (not shown) over the subcutaneous connection, undoing of the connection of the Luer lock 20, and removal of the second part 10b. A new exit-site 24 is then made, and a new second part 10b tunnelled through to the first incision for reconnection of the first 10a and (new) second 10b parts. If the infection has travelled up the original second gas line part 10b then the fresh second gas-line part is inserted through an implant tunnel that is also substantially remote from the existing implant tunnel.

Figure 2:
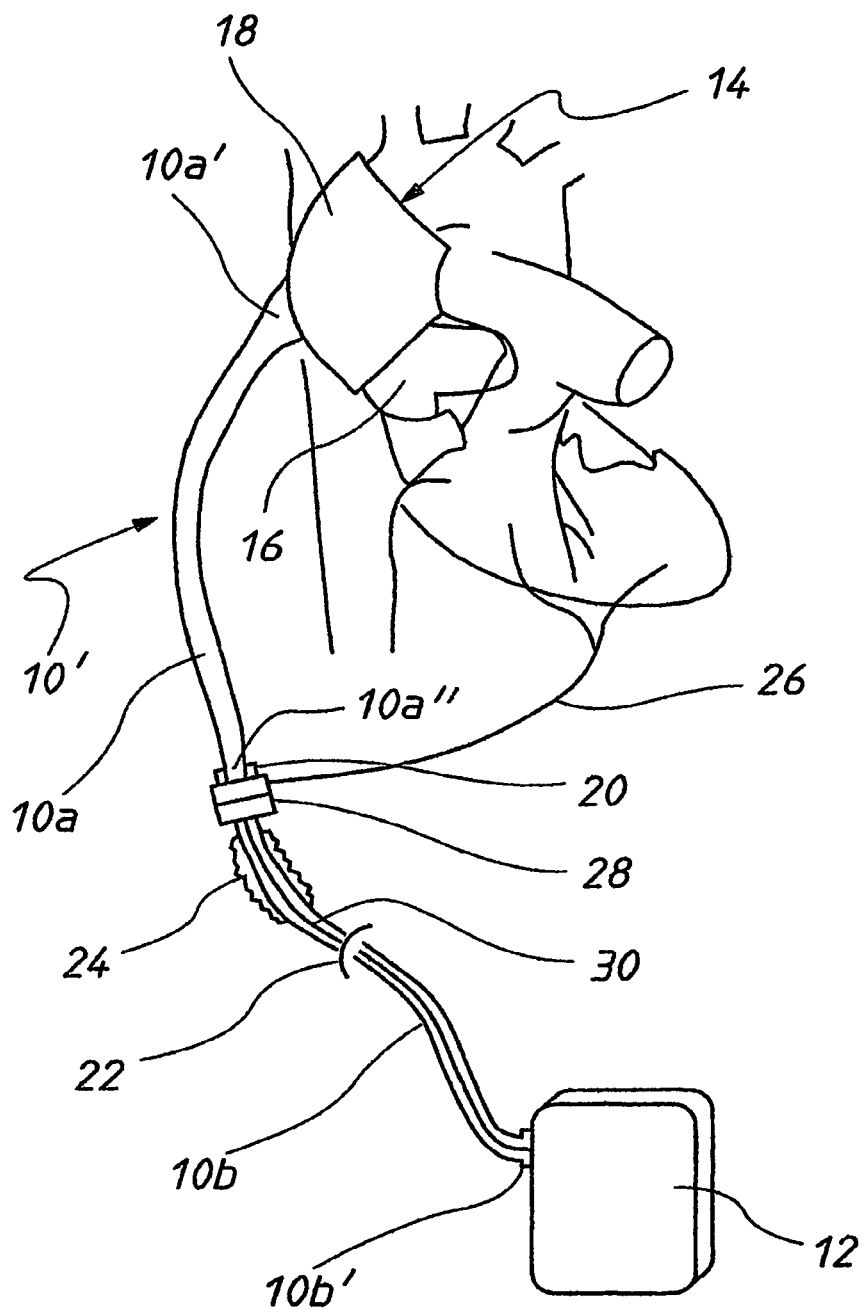
FIG. 2 is a schematic view of a percutaneous gas-line according to a second embodiment of the invention, connected between an implanted heart assist device and an external driver and in which an ECG cable is incorporated into the gas line.

FIG. 2 shows a percutaneous gas-line 10' according to a second embodiment of the invention. Like features to those of the first embodiment are indicated with like reference numerals in the second embodiment.

The gas-line 10' includes a first part (implanted) epicardial ECG lead 26, a sleeve 28 and a second part (percutaneous) ECG lead 30. The lead 26 enters the sleeve 28, which is connected between the first and second parts of the gas line 10a and 10b. The sleeve 28 has an electrical connector therein (not shown) that connects the lead 26 to an extension of the lead 30. The lead parts 26 and 30 therefore advantageously provide direct communication of ECG signals from the patient's heart to the driver 12.

The lead 30 is connected to the driver 12 and is contained within the interior of the gas-line second part 10b. Alternatively, the lead 30 can be glued to the exterior of the gas-line second part 10b. In either case, only a single exit site 22 is required, thereby minimising infection risk and patient discomfort.

It will be appreciated by the persons skilled in the art that numerous variations and/or modifications can be made to the invention as shown in the specific embodiment without departing from the spirit or scope of the invention as broadly defined. For example, the blood displacing devices are described above in relation to extra-aortic counter-pulsation but also suitable for intra aortic counter-pulsation devices, co-pulsation devices, or pneumatic driven LVADs.

What is claimed is:

1. A percutaneous interface line for an implantable medical device, the interface line comprising:
   (a) a first interface line comprising a first end configured to be sealably coupled to the medical device and a second end;
   (b) a connection fitting configured to be disposed entirely within a patient's body, wherein the connection fitting is configured to be sealably coupled to the second end of the first interface line;
   (c) a second interface line comprising:
      (i) a first end configured to be sealably and removably coupled to the connection fitting; and
      (iii) an opening defined in the first end, wherein the opening is in communication with a lumen defined within the second interface line, wherein the opening is substantially coaxial with a longitudinal axis of the interface line; and
   (d) a subcutaneous anchoring collar coupled around an outer surface along a length of at least one of the first and second interface lines, wherein the collar is configured to be disposed within the patient's body when the first end of the second interface line is coupled to the connection fitting.

2. The percutaneous interface line of claim 1, wherein the subcutaneous anchoring collar is coupled around an outer surface along a length of the first interface line.

3. The percutaneous interface line of claim 1, wherein the subcutaneous anchoring collar is coupled around an outer surface along a length of the second interface line.

4. The percutaneous interface line of claim 1, wherein the subcutaneous anchoring collar is coupled around an outer surface along a length of both the first and second interface lines.

5. The percutaneous interface line of claim 1, wherein the second interface line comprises a second end configured to be sealably and removably coupled to an external driver.

6. The percutaneous interface line of claim 1, further comprising an ECG lead incorporated into the first interface line or the second interface line, wherein the ECG lead comprises a first end configured to be coupled to a control system and a second end configured to be positioned within the patient's body.

7. The percutaneous interface line of claim 6, wherein the ECG lead is disposed within the second interface line.

8. The percutaneous interface line of claim 6, wherein the ECG lead is coupled to an exterior portion of the second interface line.

9. The percutaneous interface line of claim 6, wherein the ECG lead comprises a first part configured to be positioned within the patient's body and a second part associated with the second interface line.

10. The percutaneous interface line of claim 1, wherein the subcutaneous anchoring collar comprises a fluffy polyester.

11. The percutaneous interface line of claim 1, wherein the subcutaneous anchoring collar has a length of at least about 20 mm.

12. The percutaneous interface line of claim 1, wherein the medical device comprises a heart assist device.

13. The percutaneous interface line of claim 12, wherein the heart assist device comprises a wrap configured to be disposed around an aorta of the patient.

14. The percutaneous interface line of claim 12, wherein the hear assist device is an inflatable heart assist actuator.

15. The percutaneous interface line of claim 1, wherein the medical device comprises a left ventricular assist device.

16. The percutaneous interface line of claim 1, wherein the connection fitting comprises a Luer-lock gas-tight fitting.

17. The percutaneous interface line of claim 1, further comprising an ECG lead associated with the second interface line.

18. A percutaneous interface line for an implantable medical device, the interface line comprising:
  (a) a first interface line comprising a first end configured to be sealably coupled to the medical device and a second end;
  (b) a connection fitting configured to be disposed entirely within a patient's body, wherein the connection fitting is configured to be sealably coupled to the second end of the first interface line;
  (c) a second interface line comprising:
    (i) a first end configured to be sealably and removably coupled to the connection fitting; and
    (iii) an opening defined in the first end, wherein the opening is in communication with a lumen defined within the second interface line, wherein the opening is substantially coaxial with a longitudinal axis of the interface line; and
  (d) a subcutaneous anchoring collar coupled around an outer surface along a length of both of the first and second interface lines, wherein the collar is configured to be disposed within the patient's body when the first end of the second interface line is coupled to the connection fitting, wherein the collar has a length of at least about 20 mm.

19. The percutaneous interface line of claim 18, wherein the medical device comprises a heart assist device.

20. The percutaneous interface line of claim 18, further comprising an ECG lead associated with the second interface line.

* * * * *